United States Patent
Shih et al.

(10) Patent No.: US 9,645,213 B2
(45) Date of Patent: May 9, 2017

(54) DEVICE COMBINING MAGNETIC RESONANCE IMAGING AND POSITRON EMISSION TOMOGRAPHY FOR BREAST EXAMINATION

(71) Applicants: Ming-Chang Shih, Tainan (TW); Hung-Lung Huang, New Taipei (TW)

(72) Inventors: Ming-Chang Shih, Tainan (TW); Hung-Lung Huang, New Taipei (TW)

( * ) Notice: Subject to any disclaimer, the term of this patent is extended or adjusted under 35 U.S.C. 154(b) by 757 days.

(21) Appl. No.: 14/180,612

(22) Filed: Feb. 14, 2014

(65) Prior Publication Data
US 2015/0234022 A1    Aug. 20, 2015

(51) Int. Cl.
*G01R 33/48*     (2006.01)
*A61B 6/04*     (2006.01)
*A61B 6/03*     (2006.01)
*A61B 6/00*     (2006.01)

(52) U.S. Cl.
CPC ............ *G01R 33/481* (2013.01); *A61B 6/037* (2013.01); *A61B 6/0435* (2013.01); *A61B 6/502* (2013.01); *A61B 6/5247* (2013.01)

(58) Field of Classification Search
CPC ............................. A61B 6/5247; G01R 33/481
See application file for complete search history.

(56) References Cited

U.S. PATENT DOCUMENTS

| | | | |
|---|---|---|---|
| 6,946,841 B2 * | 9/2005 | Rubashov | G01R 33/481 324/318 |
| 2008/0071164 A1 * | 3/2008 | Pogue | A61B 5/0091 600/411 |
| 2012/0150017 A1 * | 6/2012 | Yamaya | G01R 33/3806 600/411 |
| 2013/0137964 A1 * | 5/2013 | Schellenberg | A61B 5/0555 600/411 |
| 2014/0336502 A1 * | 11/2014 | Neelakanta | A61B 5/708 600/424 |

OTHER PUBLICATIONS

BNL Newsroom, 2009. "Prototype Breast Cancer Imaging System May Improve Patient Care."*

* cited by examiner

*Primary Examiner* — Long V Le
*Assistant Examiner* — Yi-Shan Yang
(74) *Attorney, Agent, or Firm* — Rosenberg, Klein & Lee

(57) ABSTRACT

A device combining magnetic resonance imaging and positron emission tomography for a breast examination is revealed herein to comprise an air pressure source, a servo flow control module, a pedestal disposed under a breast accommodating hole of a breast MRI bed and having a bearing platform for bearing a PET scanner ring thereon, a non-metallic and non-magnetic pneumatic actuator disposed on the pedestal and connected with the servo flow control module, and a movable pulley having a first nylon rope whose one end connects to the bearing platform and the other end connects to a counterweight unit, wherein the bearing platform connects to a displacement measurement unit by a second nylon rope for receipt of a location information thereof and transmission of the same to the servo flow control module for controlling the opening of the servo flow control valve to change gas flows entering into the pneumatic actuator.

3 Claims, 4 Drawing Sheets

DEVICE COMBINING MAGNETIC RESONANCE IMAGING AND POSITRON EMISSION TOMOGRAPHY FOR BREAST EXAMINATION

BACKGROUND OF THE INVENTION

1. Field of the Invention

The present invention relates to a device combining magnetic resonance imaging (MRI) and positron emission tomography (PET) for a breast examination. The device comprises a PET scanner ring disposed in a narrow place of a breast MRI bed in order to precisely examine the breasts and acquire better images within a short time.

2. Description of Related Art

Generally, both magnetic resonance imaging (MRI) and positron emission tomography (PET) examinations are required for a subject to assist physicians in the clinical diagnosis and judgment. Magnetic resonance imaging is used to investigate the anatomy and detailed location of subjects' bodies, and positron emission tomography (PET) provides information of cell physiology and metabolism. However, there are some disadvantages respectively existed in these two medical imaging techniques, i.e. MRI is unable to offer metabolic information and disease status and PET is in lack of showing anatomy and detailed location. Moreover, these two imaging examinations cost high and take a lot of subject's time and energy in each inspection. To improve the above mentioned problems, in 2006, Philips Co. brought forward a shared and fast moveable examination bed for connecting MRI and PET to obtain complete images of a subjects' whole body. After the subject is examined by one of the two inspections, he or she can be moved instantly to receive the other one inspection. However, the move of the subject results in the image distortion, so the images need further corrections.

Currently, some researchers incorporate MRI and PET imaging for allowing a subject to be examined by both inspections simultaneously. In this technique, one must ensure in advance that both PET and relevant parts for a combination of PET and MRI can operate normally in the environments with a strong magnetic attraction and an electromagnetic interference caused by MRI. For instance, in 2010, Siemens Co. replaced the light sensitive element (a.k.a. photomultiplier, PMT) of PET with avalanche photodiodes which are unaffected by magnetic fields, so as to solve the problem of mutual influence between MRI and PET. Therefore, the Siemens PET/MRI system allows two tests to run simultaneously without moving a patient to a different scanning system. Although Siemens Co. has developed the PET/MRI system for examining subjects' whole bodies, combining a PET with a breast MRI still has a problem, i.e. difficulty in accommodating a PET machine due to the small space of a breast MRI system.

SUMMARY OF THE INVENTION

In view of the above-mentioned problems, the object of the present invention is to provide a device comprising a non-metallic and non-magnetic pneumatic actuation system combining with a servo flow control module. By a mechanism design, a platform for bearing a PET scanner ring can be placed into a narrow space of a breast MRI bed, so that the device can bear a PET scanner for positioning scanning in collaboration with a breast MRI examination. Therefore, the device can conduct a fast and accurate breast examination and the positioning accuracy thereof is less than 0.1 mm as main purposes.

Disclosed herein is a device combining magnetic resonance imaging and positron emission tomography for a breast examination. It comprises an air pressure source; a servo flow control module having a servo flow control valve for receiving gas from the air pressure source, a microcomputer for controlling the servo flow control valve, and an AD/DA interface card for receiving signals from the microcomputer; a pedestal disposed under a hole of a breast MRI bed and provided with a bearing platform mounted thereon in a sliding way for bearing a PET scanner ring, wherein the hole is provided for accommodating breasts; a counterweight unit connecting the PET scanner ring for decreasing loading weight and friction thereof, wherein the counterweight unit consists of a counterweight rope, a counterweight bar, and a first counterweight, and the counterweight rope is provided on the counterweight bar disposed on the pedestal and connects to the PET scanner ring at one end thereof and to the first counterweight at the other end thereof; a non-metallic and non-magnetic pneumatic actuator disposed on the pedestal and connected with the servo flow control module by a barometric pipe, wherein the non-metallic and non-magnetic pneumatic actuator includes a piston rod made of a Teflon® material, and the piston rod protrudes in the hole; and a movable pulley provided with a first nylon rope connecting to the bearing platform at one end thereof and connecting to a second counterweight fixed on the pedestal at the other end thereof. The bearing platform connects to a displacement measurement unit depart from a strong magnetic environment of MRI by a second nylon rope. The second nylon rope coils round an idle wheel provided on the pedestal between the bearing platform and the displacement measurement unit. The displacement measurement unit receives a location information of the bearing platform and transmits the location information to the servo flow control module for controlling the opening of the servo flow control valve to change gas flows entering into the non-metallic and non-magnetic pneumatic actuator, so that the movable pulley and the first and second nylon ropes can be driven to allow the bearing platform to move up and down under the hole.

In the foregoing description, the counterweight unit decreases friction of the first nylon rope and the loading weight of the PET scanner ring by counterweight to increase an actuation speed of the device. The displacement measurement unit is further provided with an optical scale connecting to the second nylon rope and a decoder card for receiving a pulse output from the optical scale and converting it into a location signal.

In use of a device of the present invention, a subject undergoing breast MRI is made to lie face down on a breast MRI bed with two holes for the breasts to fit in. These holes have a network of magnetic lines for the MRI to take place. Scanning position of the PET bearing platform can be modified by the servo flow control module and the displacement measurement unit. Moreover, the decreased loading weight and friction by the counterweight unit can enhance the speed of operation of the bearing platform. Accordingly, a device combines PET to the breast MRI and takes advantage of a servo flow control module, a non-metallic and non-magnetic pneumatic actuator, a movable pulley and the like to control a position of the bearing platform, so that subjects' breasts can be accurately detected within a short time.

DETAILED DESCRIPTION OF THE PREFERRED EMBODIMENT

The present invention relates to a device combining magnetic resonance imaging and positron emission tomography for a breast examination. The device comprises a PET scanner ring disposed in the narrow place of a breast MRI bed by a mechanism design approach, so as to precisely examine the breasts and acquire better images within a short time.

Hereinafter, an exemplary embodiment of the present invention will be described in detail with reference to the accompanying drawings.

Figure 1:
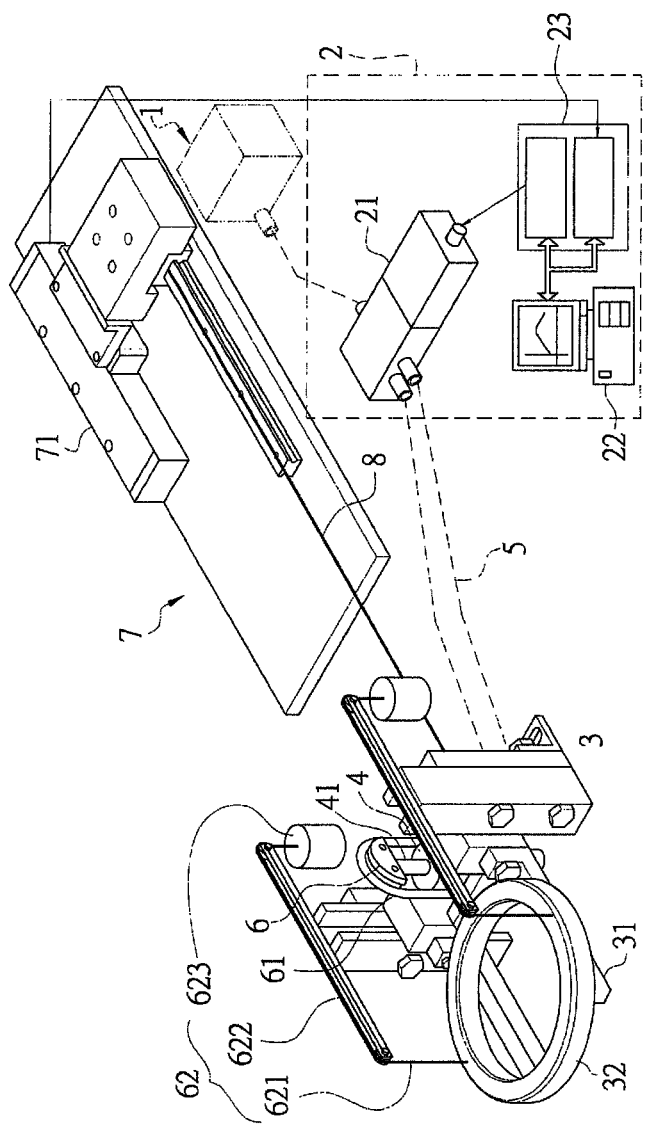
FIG. 1 is a partially enlarged diagram showing a local device structure according to the present invention.
Figure 2:
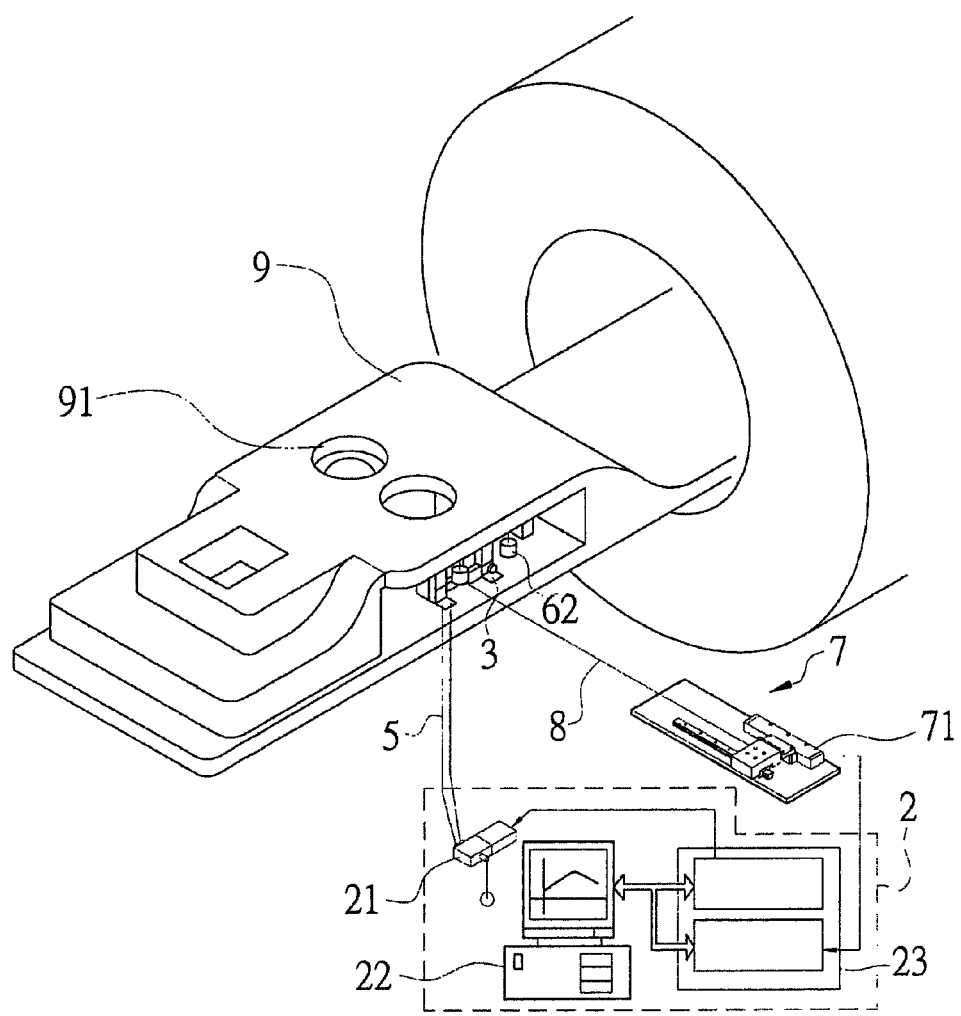
FIG. 2 is a schematic diagram showing a device combining magnetic resonance imaging and positron emission tomography for a breast examination according to the present invention.
Figure 4:
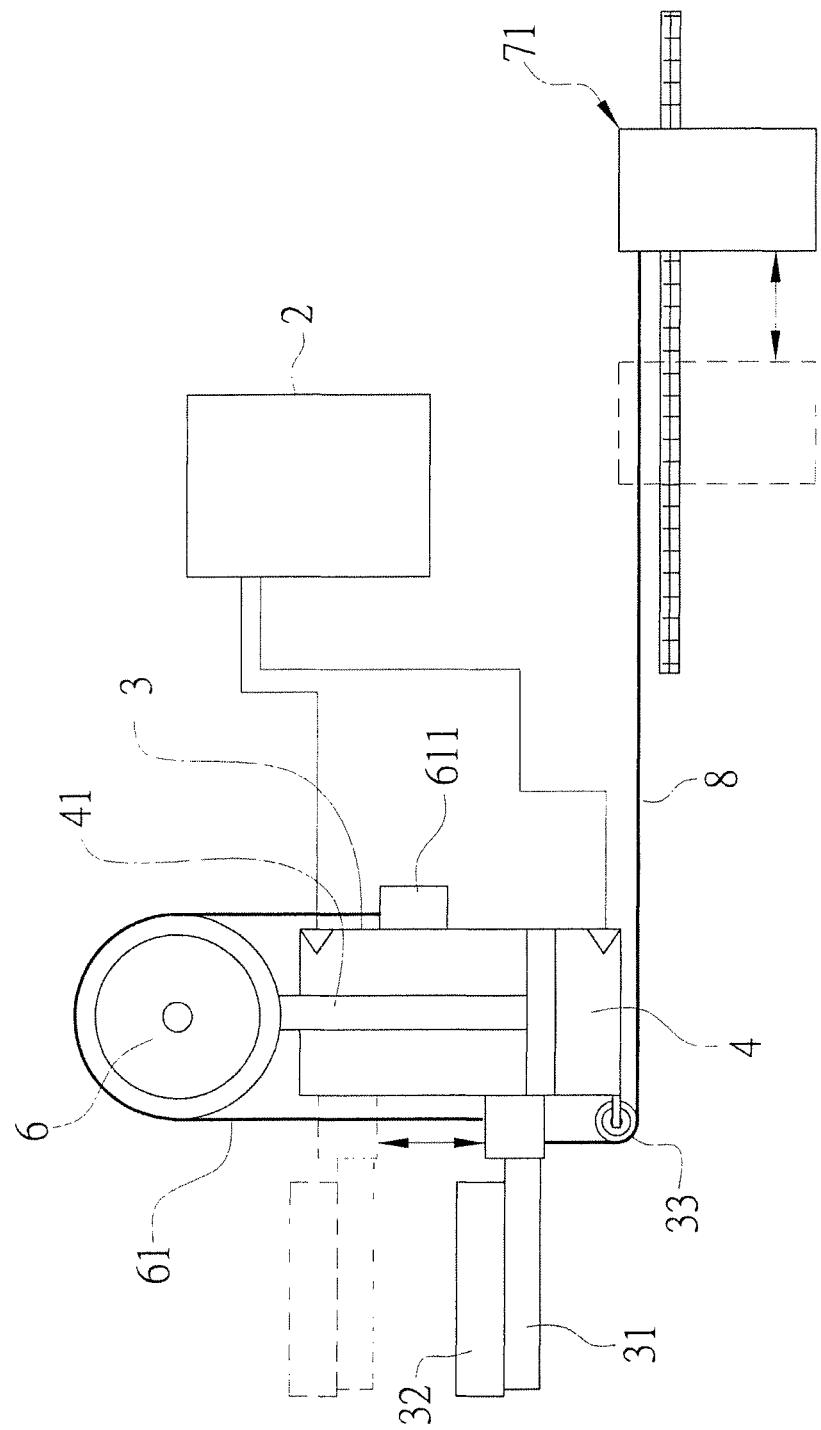
FIG. 4 is a system diagram showing a device equipped with a counterweight unit according to the present invention.

Referring to FIG. 1, FIG. 2 and FIG. 4, a partially enlarged diagram showing a local device structure according to the present invention, a schematic diagram showing a device combining magnetic resonance imaging and positron emission tomography for a breast examination according to the present invention, and a system diagram showing a device equipped with a counterweight unit according to the present invention are revealed, comprising:

an air pressure source (1);

a servo flow control module (2) including a servo flow control valve (21) for receiving gas from the air pressure source (1), a microcomputer (22) for controlling the servo flow control valve (21), and an AD/DA interface card (23) for receiving signals from the microcomputer (22);

a pedestal (3) disposed under a hole (91) of a breast MRI bed (9) and provided with a bearing platform (31) mounted in a sliding way for bearing a PET scanner ring (32) thereon, wherein the hole (91) is provided for accommodating breasts;

a counterweight unit (62) connecting the PET scanner ring (32) for decreasing loading weight and friction thereof, wherein the counterweight unit (62) consists of a counterweight rope (621), a counterweight bar (622), and a first counterweight (623), and the counterweight rope (621) is provided on the counterweight bar (622) disposed on the pedestal (3) and connects to the PET scanner ring (32) at one end thereof and to the first counterweight (623) at the other end thereof;

a non-metallic and non-magnetic pneumatic actuator (4) disposed on the pedestal (3) and connected with the servo flow control module (2) by a barometric pipe (5), wherein the non-metallic and non-magnetic pneumatic actuator (4) includes a piston rod (41) made of a Teflon® material, and the piston rod (41) is disposed in a corresponding space below the hole (91) of the breast MRI bed (9); and a movable pulley (6) provided with a first nylon rope (61) connecting to the bearing platform (31) at one end thereof and connecting to a second counterweight (611) fixed on the pedestal (3) at the other end thereof, wherein the bearing platform (31) connects to a displacement measurement unit (7) depart from a strong magnetic environment of MRI by a second nylon rope (8), the second nylon rope (8) coils round an idle wheel (33) provided on the pedestal (3) between the bearing platform (31) and the displacement measurement unit (7), and the displacement measurement unit (7) receives a location information of the bearing platform (31) and transmits the location information to the servo flow control module (2) for controlling the opening of the servo flow control valve (21) to change gas flows entering into the non-metallic and non-magnetic pneumatic actuator (4), so that the movable pulley (6) and the first and second nylon ropes (61) (8) can be driven to allow the bearing platform (31) to move up and down under the hole (91).

It is worth mentioning that the non-metallic and non-magnetic pneumatic actuator of the present invention is disclosed in the other application "non-metallic and non-magnetic pneumatic actuator" of the present inventors. All of its contents are especially incorporated herein for reference.

In use of aforesaid device, because a pedestal (3) including a bearing platform (31) and a PET scanner ring (32) is disposed in a corresponding space below the hole (91) of the breast MRI bed (9) as shown in FIG. 2, there is a maximum height limit within 15 cm. The bearing platform (31) must bear the PET scanner ring (32) to move up and down respectively about 10 cm for a breast examination. If a 10 cm-stroke pneumatic actuator is adopted herein for actuating the PET scanner ring (32) to move up and down, the extension of full portion of the piston rod (41) will exceed the height restrictions. Therefore, the present inventor designed a 5 cm-stroke non-metallic and non-magnetic pneumatic actuator (4) and combined it with a movable pulley (6) for purpose of the stroke amplification. For instance, if the non-metallic and non-magnetic pneumatic actuator (4) upward moves Py, it can drive the first nylon rope (61) through the movable pulley (6) to pull the bearing platform (31) upward moving 2 P y. Accordingly, only the 5 cm-stroke non-metallic and non-magnetic pneumatic actuator (4) used herein can cause the bearing platform (31) carrying the PET scanner ring (32) to move up and down each of 10 cm for breasts scanning.

In use of a device of the present invention, a subject has to lie face down on a breast MRI bed (9) and hang down breasts in the two holes (91). The bearing platform (31) carrying the PET scanner ring (32) is placed in the narrow space of the breast MRI bed (9). The displacement measurement unit (7) and the servo flow control module (2) can be connected by the long barometric pipe (5) and the second nylon rope (8). Because the second nylon rope (8) coils round the idle wheel (33), a horizontal force can be converted into a vertical force of the bearing platform (31) to control the scanning position of the PET scanner ring (32).

Moreover, the decreased loading weight and friction by the counterweight unit (62) can enhance the speed of operation of the bearing platform (31). Pressurized gas flows entering into the non-metallic and non-magnetic pneumatic actuator (4) can amplify the stroke by the movable pulley (6), so as to lift up or lay down the bearing platform (31).

Figure 3:
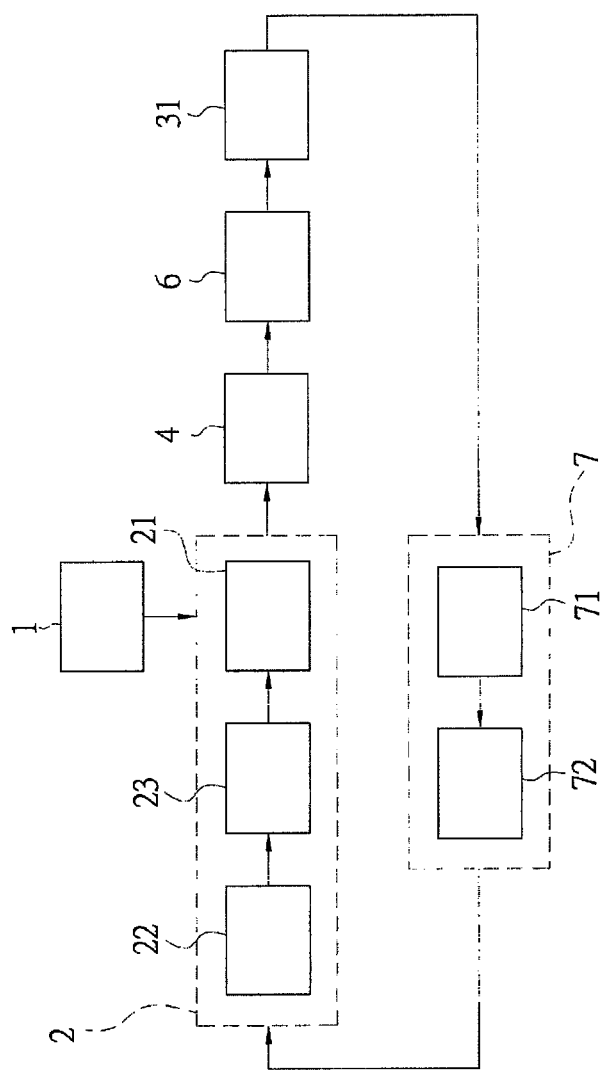
FIG. 3 is a block diagram of a device according to the present invention.

Referring to FIG. 3, a block diagram of a device according to the present invention is revealed herein. An air pressure source (1) delivers pressurized gas to a servo flow control module (2). Then a microcomputer (22) calculates a control order and send a signal to change the opening of the servo flow control valve (21) (e.g. MPYE-5-010-B from FESTO Co.) by the AD/DA interface card (23) converting the signal to an analog voltage signal. It is worth mentioning that a proportional flow control valve (MPYE-5-010-B) of FESTO Co. utilized by the present inventors is equipped with function of the servo flow control valve (21) by inventors' control method. Accordingly, pressurized gas flow and direction to the non-metallic and non-magnetic pneumatic actuator (4) disposed in the scan room or magnet room of MRI can be controlled, so that the bearing platform (31) can move upward or downward and the optical scale (71) (e.g. NCS T5C 220 from Givi Misure, with a resolution of 5 μm) shifts can simultaneously toward left or right. The location signal of the bearing platform (31) is transmitted by the second nylon rope (8) to the optical scale (71) disposed in the control room of MRI. After the location signal is decoded by a decoder card (72) (e.g. PCI-1784U) and is compared by a control order from the microcomputer (22), an error signal can be acquired and then be transmitted back to the microcomputer (22) for arithmetic processing to generate a new control signal. Therefore, the position of the PET scanner ring (32) can be controlled for accurate examination of a subject's breasts.

It is also worth mentioned that the present invention includes a displacement measurement unit (7) and a servo flow control module (2) depart from the MRI. The displacement measurement unit (7) can get a location signal of a bearing platform (31) by a nylon rope, and the position of the bearing platform (31) can be modified by the operation of a non-metallic and non-magnetic pneumatic actuator (4) controlled by the servo flow control module (2). Therefore, the devise solves the problem of magnetic interference and significantly reduce the examination time of a breast MRI and PET inspection.

What is claimed is:

1. A device combining magnetic resonance imaging (MRI) and positron emission tomography (PET) for a breast examination, comprises:
   an air pressure source;
   a servo flow control module including a servo flow control valve for receiving gas from the air pressure source,
   a microcomputer for controlling the servo flow control valve, and an analog-digital/digital-analog (AD/DA) interface card for receiving signals from the microcomputer;
   a pedestal disposed under a hole of a breast MRI bed and provided with a bearing platform mounted in a sliding way for bearing a PET scanner ring thereon, wherein the hole is provided for accommodating breasts;
   a counterweight unit connecting the PET scanner ring for decreasing loading weight and friction thereof, wherein the counterweight unit consists of a pair of counterweight ropes, a pair of counterweight bars, and a pair of first counterweights, wherein
      each of the counterweight rope is provided on each of the counterweight bar disposed on the pedestal respectively; and each of the counterweight rope connects to the PET scanner ring at one end thereof and to the respective first counterweight at the other end of the corresponding counterweight bar;
   a non-metallic and non-magnetic pneumatic actuator disposed on the pedestal and connected with the servo flow control module by a barometric pipe, wherein the non-metallic and non-magnetic pneumatic actuator includes a piston rod, and the piston rod is disposed in a corresponding space below the hole; and
   a movable pulley provided with a first nylon rope connecting to the bearing platform at one end thereof and connecting to a second counterweight fixed on the pedestal at the other end thereof, wherein the bearing platform connects to a displacement measurement unit depart from a magnetic environment of MRI by a second nylon rope, the second nylon rope coils round an idle wheel provided on the pedestal between the bearing platform and the displacement measurement unit, and the displacement measurement unit receives a location information of the bearing platform and transmits the location information to the servo flow control module for controlling an opening of the servo flow control valve to change gas flow entering into the non-metallic and non-magnetic pneumatic actuator, so that the movable pulley and the first and second nylon ropes can be driven to allow the bearing platform to move up and down under the hole.

2. The device as claimed in claim 1, wherein the counterweight unit decreases friction of the first nylon rope and the loading weight of the PET scanner ring by counterweight to increase an actuation speed of the device.

3. The device as claimed in claim 1, wherein the displacement measurement unit is provided with an optical scale connecting to the second nylon rope and a decoder card for receiving a pulse output from the optical scale and converting it into a location signal.

* * * * *